(12) United States Patent
Yu et al.

(10) Patent No.: US 10,105,362 B2
(45) Date of Patent: Oct. 23, 2018

(54) ANTI-TUMOR USE OF ANAGRELIDE AND DERIVATIVES THEREOF

(71) Applicant: SHANGHAI INSTITUTE OF MATERIA MEDICA, CHINESE ACADEMY OF SCIENCES, Shanghai (CN)

(72) Inventors: Qiang Yu, Shanghai (CN); Jing He, Shanghai (CN); Qing Zhang, Shanghai (CN)

(73) Assignee: ZHEJIANG BOSSAN PHARMACEUTICAL CO., LTD., Hangzhou, Zhejiang (CN)

( * ) Notice: Subject to any disclaimer, the term of this patent is extended or adjusted under 35 U.S.C. 154(b) by 1 day.

(21) Appl. No.: 14/916,463

(22) PCT Filed: May 16, 2014

(86) PCT No.: PCT/CN2014/077694
§ 371 (c)(1),
(2) Date: Jul. 11, 2016

(87) PCT Pub. No.: WO2014/183673
PCT Pub. Date: Nov. 20, 2014

(65) Prior Publication Data
US 2017/0143717 A1   May 25, 2017

(30) Foreign Application Priority Data
May 16, 2013  (CN) .......................... 2013 1 0180849

(51) Int. Cl.
*A61K 31/5025* (2006.01)
*C12N 5/09* (2010.01)

(52) U.S. Cl.
CPC ........ *A61K 31/5025* (2013.01); *C12N 5/0693* (2013.01); *C12N 2501/06* (2013.01)

(58) Field of Classification Search
CPC ............ A61K 31/5025; C12N 2501/06; C12N 5/0693
See application file for complete search history.

(56) References Cited

U.S. PATENT DOCUMENTS

2004/0180812 A1    9/2004 Dicker et al.

FOREIGN PATENT DOCUMENTS

| JP | 2004051594 | 2/2004 |
| WO | 2013019058 | 2/2013 |

OTHER PUBLICATIONS

Wolff (Medicinal Chemistry) summarizes the state of the prodrug art. Wolff, Manfred E. "Burger's Medicinal Chemistry, 5ed, Part I", John Wiley & Sons, 1995, pp. 975-977.*
Anderson (Chem and Biol 10:787-797, 2003).*
Thiel (Nature Biotechnol 2:513-519, 2004), "libraries are small and hit rates are on the order of one in ten" (p. 517, col. 2).*

(Continued)

*Primary Examiner* — Savitha M Rao
(74) *Attorney, Agent, or Firm* — Hamre, Schumann, Mueller & Larson, P.C.

(57) ABSTRACT

The present invention provides an anti-tumor use of Anagrelide and derivatives thereof and, more specifically, the present invention provides the use of Anagrelide and derivatives thereof in the preparation of pharmaceuticals or pharmaceutical compositions for the treatment or inhibition of tumors.

6 Claims, 7 Drawing Sheets

(56) References Cited

OTHER PUBLICATIONS

Ando et al. (Remington Pharmaceutical sciences, 20th edition, copyright 2000, pp. 704-712.*
International Search Report for international application No. PCT/CN2014/077694, dated Aug. 20, 2014 (4 pages, including English translation).

* cited by examiner

ANTI-TUMOR USE OF ANAGRELIDE AND DERIVATIVES THEREOF

FIELD OF THE INVENTION

The present invention relates to pharmaceutical filed, and specifically, the present invention provides the anti-tumor use of Anagrelide and the derivatives thereof.

BACKGROUND OF THE INVENTION

Cancer has become the second major disease threatening people's health. However, people do not have any good method for treatment of cancer. It is known that there are over 30,000 genes in human genome, while there are about 200 targets for drugs. The number of theoretical targets predicted on basis of genome is about 2000, while there are about 10,000 medicines available in clinical in about 1200 different structure types. Therefore, now there are a large number of compounds targeting at various target proteins of different functions and structures in human body. Furthermore, these commercially available drugs have demonstrated to have a confirmed safety and good bioavailability.

Anagrelide, also known as Agrylin, whose structural formula is 6,7-dichloro-1,5-dihydro-imidazo [2,1-b] quinazolin-2 (3H)-one, came into the market in March of 1997 in US as a phosphodiesterase inhibitor useful for treatment of anti-thrombocythemia. As early as in 1979, US scientists J. S. Fleming and J. P. Buyniski found a novel small molecule compound BL-4162A (Anagrelide) exhibited a significant anti-thrombotic function in animal experiments. Subsequent studies disclosed that Anagrelide was capable of inhibiting phosphodiesterase (PDE) activity, increasing intracellular cAMP content, thus affecting blood cell functions such as proliferation, maturation, and differentiation. However, functions and applications of Anagrelide in the treatment of tumor have not been reported. Therefore, there is no application of Anagrelide or the derivatives thereof in treatment of tumor.

Since there is absence of satisfying and effective tumor treating method, the development of a novel anti-tumor medicine is urgently needed in the field.

SUMMARY OF THE INVENTION

The present invention has provided a new use of Anagrelide or the derivatives in the treatment of tumor.

In the first aspect of the present invention, it provides a use of a compound of Formula I, an optical isomer, or a pharmaceutically acceptable salt or a prodrug thereof in preparation of a medicine or a pharmaceutical composition for treatment or inhibition of tumor and/or inhibition of growth of tumor cells;

(I)

wherein:
each of $R_1$, $R_2$, $R_3$, $R_4$, $R_5$, $R_6$, $R_7$ and $R_8$ is independently selected from the group consisting of: hydrogen atom, halogen atom, amino group, hydroxyl group, cyano group, aldehyde group, nitro group, carboxyl group, substituted or unsubstituted C1-C10 alkyl group, substituted or unsubstituted C3-C10 cycloalkyl group, substituted or unsubstituted C2-C10 alkenyl group, substituted or unsubstituted C2-C10 alkynyl group, substituted or unsubstituted C6-C10 aryl group, substituted or unsubstituted C1-C10 heteroaryl group, substituted or unsubstituted C1-C10 alkoxy group, substituted or unsubstituted C6-C10 aryloxy group, substituted or unsubstituted C1-C10 heteroaryloxy group, substituted or unsubstituted C1-C10 acyl group, substituted or unsubstituted C1-C10 ester group, and substituted or unsubstituted C1-C10 sulfonyl;

or $R_1$ and $R_2$ together form, and/or $R_3$ and $R_4$ together form a group selected from the group consisting of: substituted or unsubstituted C3-C20 cycloalkyl, substituted or unsubstituted C1-C20 hetrocycloalkyl, and =O;

$R_9$ is selected from the group consisting of: hydrogen atom, hydroxy, substituted or unsubstituted C1-C10 alkyl group, substituted or unsubstituted C3-C10 cycloalkyl group, substituted or unsubstituted C6-C10 aryl group, substituted or unsubstituted C1-C10 heteroaryl group, substituted or unsubstituted C1-C10 alkoxy group, substituted or unsubstituted C6-C10 aryloxy group, substituted or unsubstituted acyl group, and substituted or unsubstituted C1-C10 sulfonyl;

wherein the term "substituted" refers to one or more hydrogen atoms in the group are substituted by one or more substituents selected from the group consisting of: C1-C10 alkyl group, C3-C10 cycloalkyl group, C1-C10 alkoxy, halogen, hydroxy, carboxyl, C1-C10 aldehyde group, C2-C10 acyl group, C2-C10 ester group, amino group, and phenyl group;

the phenyl comprises unsubstituted or substituted phenyl with 1-3 substituents selected from the group consisting of: halogen, C1-C10 alkyl, cyano group, OH, nitro group, C3-C10 cycloalkyl, C1-C10 alkoxy, and amino group.

In another preferred embodiment, $R_1$, $R_2$, $R_3$, $R_4$, $R_5$, $R_6$, $R_7$ and $R_8$ are independently selected from the group consisting of: hydrogen atom, halogen atom, amino group, hydroxyl group, cyano group, nitro group, amino group, aldehyde group, carboxyl group, substituted or unsubstituted C1-C5 alkyl group, substituted or unsubstituted C3-C6 cycloalkyl group, substituted or unsubstituted C2-C5 alkenyl group, substituted or unsubstituted C2-C5 alkynyl group, substituted or unsubstituted C6-C10 aryl group, substituted or unsubstituted C1-C6 heteroaryl group, substituted or unsubstituted C1-C5 alkoxy group, substituted or unsubstituted C6-C10 aryloxy group, substituted or unsubstituted C1-C6 heteroaryloxy group, substituted or unsubstituted —CO—C1-C5 alkyl, substituted or unsubstituted C1-C5 alkyl-COO—, substituted or unsubstituted C1-C5 sulfonyl;

or $R_1$ and $R_2$, or $R_3$ and $R_4$ together form a group selected from the group consisting of: substituted or unsubstituted C3-C10 cycloalkyl, substituted or unsubstituted C1-C10 hetrocycloalkyl, and carbonyl;

$R_9$ is selected from the group consisting of: hydrogen atom, hydroxy, substituted or unsubstituted C1-C5 alkyl group, substituted or unsubstituted C3-C6 cycloalkyl group, substituted or unsubstituted C6-C10 aryl group, substituted or unsubstituted C1-C10 heteroaryl group, substituted or unsubstituted C1-C5 alkoxy group, substituted or unsubstituted C6-C10 aryloxy group, substituted or unsubstituted —CO—C1-C5 alkyl group, substituted or unsubstituted C1-C5 sulfonyl;

wherein the definition of "substituted" is defined as above.

In another preferred embodiment, each of $R_1$ to $R_8$ is independently selected from the group consisting of: hydrogen atom, halogen atom, cyano group, substituted or unsubstituted C1-C5 alkyl group, substituted or unsubstituted C1-C5 alkoxy group, and substituted or unsubstituted C3-C6 cycloalkyl;

or $R_1$ and $R_2$ together form, and/or $R_3$ and $R_4$ together form a group selected from the group consisting of: substituted or unsubstituted C1-C5 cycloalkyl, substituted or unsubstituted C1-C5 hetrocyclo alkyl, and carbonyl;

$R_9$ is selected from the group consisting of: hydrogen atom, substituted or unsubstituted C1-C5 alkyl group, and substituted or unsubstituted C3-C6 cycloalkyl;

wherein the definition of "substituted" is defined as above.

In another preferred embodiment, 1-8 of $R_1$ to $R_9$ are hydrogen atom, and preferably 2-7 of $R_1$ to $R_9$ are hydrogen groups.

In another preferred embodiment, 1-8 of $R_1$ to $R_8$ are halogen atom.

In another preferred embodiment, 1-8 of $R_1$ to $R_8$ are halogen atom, and the rest of $R_1$ to $R_8$ are hydrogen atom.

In another preferred embodiment, the compound of Formula I has a structure of Formula II:

(II)

In another preferred embodiment, the compound of Formula I has a structure selected from the group consisting of:

In another preferred embodiment, the pharmaceutically acceptable salt is selected from the group consisting of: hydrochloride, acetate, phosphate, or combinations thereof.

In another preferred embodiment, the pharmaceutical compositions comprises: (a) a therapeutically effective amount of Anagrelide; and (b) a pharmaceutically acceptable carrier.

In another preferred embodiment, the effective concentration of Anagrelide is 0.01 nM/L-1 mM/L, preferably 0.1 nM/L-500 µM/L, and most preferably 1 nM/L-100 µM/L.

In another preferred embodiment, the content of Anagrelide in the pharmaceutical composition is 0.01-99 wt %, and preferably 0.1-90 wt %.

In another preferred embodiment, the medicine or pharmaceutical composition is used to induce tumor cell apoptosis.

In another preferred embodiment, the medicine or pharmaceutical composition is used to disturb proliferation of tumor cell.

In another preferred embodiment, the medicine or pharmaceutical composition is used to adjust cell cycle of tumor cells; and/or the medicine or pharmaceutical composition is used to block cell cycle of tumor cells.

In another preferred embodiment, the medicine or pharmaceutical composition is used to induce arrest of tumor cells in G1 or G2 cycle.

In another preferred embodiment, the medicine or pharmaceutical composition is used to inhibit metastasis of tumor cell.

In another preferred embodiment, the tumor or tumor cell is selected from the group consisting of: liver cancer, cervical cancer, glioma, colon cancer, kidney cancer, breast cancer, lung cancer, prostate cancer, pancreatic cancer, skin cancer, nasopharyngeal cancer, esophageal cancer, gastric cancer, ovarian cancer, and melanoma.

In another preferred embodiment, the cancer cell is selected from the group consisting of: Hela, H4, FHCC98, SMMC7721, BEL7404, A498, SW1116, MDA-MB-231, MDA-MB-468, DU145, U87-MG, Wi38, H1299, or combinations thereof.

In another preferred embodiment, the cancer cell is selected from the group consisting of: Hela, H4, FHCC98, SMMC7721, or combinations thereof.

In the second aspect of the present invention, it provides a cell cycle retardant, the retardant comprises an effective amount of compounds of Formula I, or a pharmaceutically acceptable salt or a prodrug thereof, or a pharmaceutical composition thereof.

In another preferred embodiment, the compound of Formula I is Anagrelide.

In another preferred embodiment, the retardant is used to induce the G1, G2 cycle arrest of tumor cells.

In another preferred embodiment, the retardant further comprises a carrier.

In another preferred embodiment, the carrier is a pharmaceutically acceptable carrier.

In the third aspect of the present invention, it provides an in vitro non-therapeutic method to regulate cell cycle, which comprises the following step: cultivating a cell in a culture system comprising an effective amount of a compound of Formula I, or a pharmaceutically acceptable salt or a prodrug thereof, or a pharmaceutical composition thereof.

In another preferred embodiment, the compound of Formula I is Anagrelide.

In another preferred embodiment, the cell is cultivated in a culture system comprising an effective amount of Anagrelide hydrochloride.

In another preferred embodiment, the cell is tumor cell, and the tumor cell is selected from: liver cancer, cervical cancer, glioma, colon cancer, kidney cancer, breast cancer, lung cancer, prostate cancer, pancreatic cancer, skin cancer, nasopharyngeal cancer, esophageal cancer, gastric cancer, ovarian cancer, or melanoma.

In another preferred embodiment, the cancer cell is selected from the group consisting of: Hela, H4, FHCC98, SMMC7721, BEL7404, A498, SW1116, MDA-MB-231, MDA-MB-468, DU145, U87-MG, Wi38, H1299, and combinations thereof; more preferably is selected from the group consisting of: Hela, H4, FHCC98, SMMC7721, and combinations thereof.

In another preferred embodiment, the effective concentration of a compound of Formula I compound or its pharmaceutically acceptable salt or its prodrug is 0.01 nM/L-1 mM/L, preferably 0.1 nM/L-500 μM/L, and most preferably 1 nM/L-100 μM/L.

In another preferred embodiment, the action period of compound of Formula I is 2-96 h.

In another preferred embodiment, the action period of compound of Formula I is 1-30 days.

In the fourth aspect of the present invention, it provides an in vitro non-therapeutic method to inhibit cell growth or to induce apoptosis, which comprises the following step: cultivating a cell in a culture system comprising an effective amount of compounds of Formula I, or a pharmaceutically acceptable salt or a prodrug thereof, or a pharmaceutical composition thereof.

In another preferred embodiment, the compound of Formula I is Anagrelide.

In another preferred embodiment, the cell is tumor cell.

In another preferred embodiment, the effective concentration of a compound of Formula I is 0.01 nM/L-1 mM/L, preferably 0.1 nM/L-500 μM, and most preferably 1 nM/L-100 μM.

In another preferred embodiment, when used in vitro, the action period of compound of Formula I is 2-96 h.

In another preferred embodiment, when used in vitro, the action period of compound of Formula I is 1-360 days, preferably 1-180 days, more preferably 1-60 days, and most preferably 1-30 days.

In the fifth aspect of the present invention, it provides a method to prepare an anti-tumor medicine, wherein the method comprises: mixing an effective amount of a compound of Formula I, oral pharmaceutically acceptable salt or a prodrug thereof with a pharmaceutically acceptable carrier, thereby forming a pharmaceutical composition.

In another preferred embodiment, the compound of Formula I is Anagrelide.

In another preferred embodiment, the composition further comprises the following ingredients: a tumor inhibitor, a tumor apoptosis inducer, or combinations thereof.

In the sixth aspect of the present invention, it provides a method for treating cancer, which comprises: administrating a therapeutically effective amount of a compounds of Formula I, or a pharmaceutically acceptable salt or a prodrug thereof, or a pharmaceutical composition thereof to a subject in need.

In the seventh aspect of the present invention, it provides a pharmaceutical composition for treatment of cancer, wherein the pharmaceutical composition comprises:
(a) a pharmaceutically acceptable carrier, and (b) a compound of Formula I, or a pharmaceutically acceptable salt or a prodrug thereof.

(I)

wherein each of the groups is defined as above.

In another preferred embodiment, the composition is in oral dosage form or injection form.

In the eighth aspect of the present invention, it provides a use of compound of Formula I, an optical isomer, or a pharmaceutically acceptable salt or a prodrug thereof in preparation of a composition, wherein the composition is used to (i) inhibit growth of tumor cells; (ii) induce tumor cell apoptosis; (iii) interfere tumor cell proliferation; (iv) regulate cell cycle of tumor cells; (v) induce G1, G2 cycle arrest in tumor cells; and/or (vi) inhibit metastasis of tumor cells.

In another preferred embodiment, the composition is a pharmaceutical composition.

It should be understood that, in the present invention, each of the technical features specifically described above and below (such as those in the Examples) can be combined with each other, thereby constituting new or preferred technical solutions which need not be specified again herein.

DESCRIPTION OF THE DRAWINGS

FIG. 2 shows the spectrum of inhibition on tumor cells growth of Anagrelide, wherein:

FIG. 2A shows the tumor growth inhibition spectrum of 1 μM Anagrelide;

FIG. 2B shows the tumor growth inhibition spectrum of 50 μM Anagrelide;

FIG. 11 shows the effect of Anagrelide on the blood routine test of tumor-bearing nude mice; wherein, FIG. 11A shows the effect of Anagrelide on leukocyte;

FIG. 11B shows the effect of Anagrelide on erythrocyte; and

FIG. 11C shows the effect of Anagrelide on hemoglobin;

FIG. 11D shows the effect of Anagrelide on blood platelet.

In FIGS. 8-11, model represents model animal group, Anagrelide I represents administrating group I in which the dosage of administration was 10 mg/kg, and Anagrelide II represents administrating group II in which the dosage of administration was 30 mg/kg.

EMBODIMENTS FOR CARRYING OUT THE INVENTION

Through long and intensive study, by screening a large number of compounds, the applicant has unexpectedly found for the first time that Anagrelide, a conventional commercially available for the treatment of thrombocythemia anti-drug, can be used to treat cancer, can inhibit tumor cell growth and can change cell cycle, and has shown an excellent effect in inhibiting tumor cell growth and inducing tumor cell death. The present invention is completed on basis of this discovery.

Terms

As used herein, the term "substituted" refers to one or more hydrogen atoms in a group are substituted by a substituent selected from the group consisting of: C1-C10 alkyl group, C3-C10 cycloalkyl group, C1-C10 alkoxy, halogen, hydroxy, carboxy (—COOH), C1-C10 aldehyde group, C2-C10 acyl group, C2-C10 ester group, amino group, phenyl group; wherein the phenyl includes unsubstituted phenyl or phenyl substituted by 1-3 substituents, wherein the substituents are selected from: halogen, C1-C10 alkyl, cyano, OH, nitro group, C3-C10 cycloalkyl group, C1-C10 alkoxy, or amino.

As used herein, the term "C1-C10 alkyl" refers to linear or branched alkyl with 1 to 10 carbon atoms, such as methyl, ethyl, propyl, isopropyl, butyl, isobutyl, sec-butyl, tert-butyl, or similar groups.

The term "C3-C10 cycle alkyl" refers to a cyclic alkyl with 3 to 10 carbon atoms, such as cyclopropyl, cyclobutyl, cyclopentyl, cycloheptyl, or the like.

The term "C2-C10 alkenyl group" means an alkenyl group having 2 to 10 carbon atoms, e.g., ethenyl, propenyl, isopropenyl, butenyl, isobutenyl, sec-butenyl, tertiary butenyl, or the like.

The term "C2-C10 alkynyl" refers to an alkynyl group having 2 to 10 carbon atoms, e.g., ethynyl, propynyl, isoalkynyl group, butynyl group, alkynyl isobutyl, sec-butynyl, t-butynyl group, or the like.

The term "C6-C10 aryl" refers to an aryl with 6 to 10 carbon atoms, such as monocyclic or bicyclic aryl, such as phenyl, naphthyl, or the like.

The term "C1-C10 heteroaryl" refers to a heteroaryl group with 1 to 10 carbon atoms, such as pyrrolyl, pyridyl, furyl, or the like.

The term "C1-C10 alkoxy" refers to a straight or branched chain alkyl group having 1 to 10 carbon atoms, such as methoxy, ethoxy, propoxy, isopropoxy, butoxy, iso-butoxy, sec-butoxy, tert-butoxy, or the like.

The term "C6-C10 aryloxy" refers to a straight chain or branched aryloxy group having 6-10 carbon atoms, such as phenyloxy, naphthyloxy, or the like.

The term "C1-C10 heteroaryloxy" refers to a straight chain or branched heteroaryloxy group having 1-10 carbon atoms, such as pyridyloxy, furyloxy, or the like.

Terms "C1-C10 acyl group" refers to a groups which has a "—CO-alkyl" structure, and preferably "—CO—C1-C10 alkyl", such as formyl group, acetyl group, propionyl group, isopropionyl group, butyryl group, isobutyryl group, sec-butyryl group, tert-butyryl group, or the like.

The term "C1-C10 ester group" refers to a group which has an "alkyl-COO—" structure, and preferably a C1-C10 alkyl-COO— structure, such as CH₃COO—, C₂H₅COO—, C₃H₈COO—, (CH₃)₂CHCOO—, nC₄H₉COO—, tC₄H₉COO—, or the like.

Terms "C1-C10 sulfonyl" refers to a group which has a "—SO₂-alkyl" structure, and preferably "—SO₂—C1-C10 alkyl", such as methylsulfonyl, ethylsulfonyl, propylsulfonyl, isopropylsulfonyl, butylsulfonyl, isobutylsulfonyl, sec-butylsulfonyl, tert-butylsulfonyl, or the like.

The term "C1-C20 heterocycloalkyl group" means a heterocyclic group having 1 to 20 carbon atoms, such as ethyloxide, tetrahydrofuryl, pyrrolidine group, or the like.

The term "halogen" refers to F, Cl, Br and I.

Anagrelide and Use Thereof

As used herein, terms "Anagrelide", "Agrylin" and "ANA" can be used interchangeably, and all refers to a compound of the following formula, or the pharmaceutically acceptable salts or prodrugs thereof, or in a form of formulation:

In a preferred embodiment of the present invention, the Anagrelide is 6,7-dichloro-1,5-dihydro-imidazo [2,1-b] quinazolin-2 (3H)-one.

Currently, Anagrelide is used as a phosphodiesterase inhibitor in clinical for the treatment of anti-thrombocythemia. The present invention provides a new use of Anagrelide or a pharmaceutically acceptable formulation thereof in inhibition of tumor. Specifically, the present invention provides the following new uses:

(a) used as an anticancer drug for the treatment or inhibition of cancer or tumor;

(b) used for the in vitro or in vivo selective inhibition of proliferation of tumor cells, or inducing apoptosis;

(c) used to selectively in vivo or in vitro regulate cell cycle, induce G1 and G2 cycle arrest of cells;

(b) used to in vitro or in vivo inhibit the proliferation of tumor cells selectively.

The Anagrelide or the pharmaceutical composition can be used in relatively low dosage, and preferably, the Anagrelide can be used at a concentration≤1 mM/L to a cell, and provide the desired effects.

Use of Derivatives of Anagrelide

The present invention also provides a use of a type of Anagrelide derivatives, an optical isomer, or a pharmaceutically acceptable salt or a prodrug thereof, wherein the derivative has the following Formula I structure:

wherein:

each of $R_1$-$R_8$ is independently selected from the group consisting of: hydrogen atom, halogen atom, amino group, hydroxyl group, cyano group, aldehyde group, nitro group, carboxyl group (—COOH), substituted or unsubstituted C1-C10 alkyl group, substituted or unsubstituted C3-C10 cycloalkyl group, substituted or unsubstituted C2-C10 alkenyl group, substituted or unsubstituted C2-C10 alkynyl group, substituted or unsubstituted C6-C10 aryl group, substituted or unsubstituted C1-C10 heteroaryl group (e.g., substituted or unsubstituted 5-membered or 6-membered hetero ring, 8- to 10-membered heteroaromatic bicyclic ring system), substituted or unsubstituted C1-C10 alkoxy group, substituted or unsubstituted C6-C10 aryloxy group, substituted or unsubstituted C1-C10 heteroaryloxy group, substituted or unsubstituted acyl group (preferably —CO—C1-C10 alkyl), substituted or unsubstituted ester group (preferably C1-C10 alkyl-COO-), and substituted or unsubstituted C1-C10 sulfonyl (—$SO_2$—C1-C10 alkyl);

or $R_1$ and $R_2$, or $R_3$ and $R_4$ together form the following groups: substituted or unsubstituted C3-C20 cycloalkyl (preferably C3-C10 cycloalkyl), substituted or unsubstituted C1-C20 hetrocyclo alkyl (preferably substituted or unsubstituted 5-membered or 6-membered hetero ring, 8- to 12-membered heteroaromatic bicyclic ring system), or carbonyl (=O);

$R_9$ is selected from the group consisting of: hydrogen atom, hydroxy, substituted or unsubstituted C1-C10 alkyl group, substituted or unsubstituted C3-C10 cycloalkyl group, substituted or unsubstituted C6-C10 aryl group, substituted or unsubstituted C1-C10 heteroaryl group, substituted or unsubstituted C1-C10 alkoxy group, substituted or unsubstituted C6-C10 aryloxy group, substituted or unsubstituted acyl group (preferably —CO—C1-C10 alkyl), and substituted or unsubstituted C1-C10 sulfonyl;

wherein term "substituted" refers to one or more hydrogen atoms in the group are substituted by the following substituents: C1-C10 alkyl group, C3-C10 cycloalkyl group, C1-C10 alkoxy, halogen, hydroxy, carboxy (—COOH), C1-C10 aldehyde group, C2-C10 acyl group, C2-C10 ester group, amino group, phenyl group;

the phenyl comprises unsubstituted or substituted phenyl with 1-3 substituents, and the substituents are selected from the group consisting of: halogen, C1-C10 alkyl, cyano group, OH, nitro group, C3-C10 cycloalkyl, C1-C10 alkoxy, and amino group.

In another preferred embodiment, each of $R_1$-$R_8$ is independently selected from the group consisting of: hydrogen atom, halogen atom, amino group, hydroxyl group, cyano group, nitro group, amino group, aldehyde group, carboxyl group, substituted or unsubstituted C1-C5 alkyl group, substituted or unsubstituted C3-C6 cycloalkyl group, substituted or unsubstituted C2-C5 alkenyl group, substituted or unsubstituted C2-C5 alkynyl group, substituted or unsubstituted C6-C10 aryl group, substituted or unsubstituted C1-C6 heteroaryl group, substituted or unsubstituted C1-C5 alkoxy group, substituted or unsubstituted C6-C10 aryloxy group, substituted or unsubstituted C1-C6 heteroaryloxy group, substituted or unsubstituted —CO—C1-C5 alkyl, substituted or unsubstituted C1-C5 alkyl-COO—, and substituted or unsubstituted C1-C5 sulfonyl; or R1 and R2, or R3 and R4 together form the following groups: substituted or unsubstituted C3-C10 cycloalkyl, substituted or unsubstituted C1-C10 hetrocyclo alkyl, or carbonyl;

$R_9$ is selected from the group consisting of: hydrogen atom, hydroxy, substituted or unsubstituted C1-C5 alkyl group, substituted or unsubstituted C3-C6 cycloalkyl group, substituted or unsubstituted C6-C10 aryl group, substituted or unsubstituted C1-C10 heteroaryl group, substituted or unsubstituted C1-C5 alkoxy group, substituted or unsubstituted C6-C10 aryloxy group, substituted or unsubstituted —CO—C1-C5 alkyl group, and substituted or unsubstituted C1-C5 sulfonyl;

wherein the definition of "substituted" is defined as above.

In another preferred embodiment, each of $R_1$-$R_8$ is independently selected from the group consisting of: hydrogen atom, halogen atom, cyano group, substituted or unsubstituted C1-C5 alkyl group, and substituted or unsubstituted C3-C6 cycloalkyl;

or $R_1$ and $R_2$, or $R_3$ and $R_4$ together forms the following groups: substituted or unsubstituted C1-C5 cycloalkyl, substituted or unsubstituted C1-C5 hetrocyclo alkyl, or carbonyl;

$R_9$ is selected from the group consisting of: hydrogen atom, substituted or unsubstituted C1-C5 alkyl group, and substituted or unsubstituted C3-C6 cycloalkyl;

wherein the definition of "substituted" is defined as above.

In another preferred embodiment, 1-8 of $R_1$ to $R_9$ are hydrogen, preferably 2-7 of $R_1$ to $R_9$ are hydrogen.

In another preferred embodiment, 1-8 of $R_1$ to $R_8$ are halogen.

In another preferred embodiment, 1-8 of $R_1$ to $R_8$ are halogen, and the others of $R_1$-$R_8$ are hydrogen.

In another preferred embodiment, the compound of Formula I has the structure of Formula II:

In another preferred embodiment, the compound of Formula I has a structure selected from the group consisting of:

In another preferred embodiment, the pharmaceutically acceptable salt is selected from the group consisting of: hydrochloride, acetate, phosphate, and combinations thereof.

The present invention provides a new use of compound of Formula I or a pharmaceutically acceptable salt or a prodrug, or a pharmaceutically acceptable formulation thereof in inhibition of tumor. Specifically, the present invention provides the following new uses:

(a) used as an anticancer drug for the treatment or inhibition of cancer or tumor;

(b) used for the in vitro or in vivo selective inhibition of proliferation of tumor cells, or inducing apoptosis;

(c) used to selectively in vivo or in vitro regulate cell cycle, induce G1 and G2 cycle arrest of cells;

(b) used to in vitro or in vivo inhibit the proliferation of tumor cells selectively.

Pharmaceutically Acceptable Salts or Prodrugs

As used herein, the term "pharmaceutically acceptable salts" refers to salts formed by a compound of the present invention with a pharmaceutically acceptable inorganic or organic acids, wherein the inorganic acids include: hydrochloric acid, hydrobromic acid, phosphoric acid, nitric acid, sulfuric acid; the organic acids include: formic acid, acetic acid, propionic acid, succinic acid, naphthalene disulfonic acid (1,5), asiatic acid, oxalic acid, tartaric acid, lactic acid, salicylic acid, benzoic acid, diethyl acetate acid, malonic acid, succinic acid, fumaric acid, pimelic acid, adipic acid, maleic acid, malic acid, sulfamic acid, phenylpropionic acid, gluconic acid, ascorbic acid, nicotinic acid, isonicotinic acid, methanesulfonic acid, p-toluenesulfonic acid, citric acid, and amino acids.

As used herein, the term "pharmaceutically acceptable prodrug" means a compound inactive in vitro, but can be converted into the active substance of the Formula I in vivo, thus exerting the pharmacological activity.

Pharmaceutical Composition

The present invention also provides a pharmaceutical composition which has a significant anti-tumor effect. The composition comprises a therapeutically effective acceptable amount of a compound of the Formula I, or a pharmaceutically acceptable salt thereof, and one or more pharmaceutically acceptable carriers. In another preferred embodiment, the pharmaceutical compositions comprises a therapeutically effective amount of Anagrelide hydrochloride, and one or more pharmaceutically acceptable carriers.

The mixture of the compound or the pharmaceutically acceptable salts thereof and pharmaceutically acceptable excipients, diluents can be administrated in tablet, capsule, granule, powder or syrup forms for oral administration, or in injection formulations for non-oral administration. In the present invention, the pharmaceutical compositions preferably comprises 0.01%-99% by weight of a compound of Formula I or salts thereof as an active ingredient, and more preferably 0.1%-90% by weight of active ingredient.

The above formulations may be prepared by conventional pharmacy methods. Examples of acceptable adjuvants can be used include excipients (e.g. sugar derivatives such as lactose, sucrose, glucose, mannitol and sorbitol; starch derivatives such as corn starch, potato starch, dextrin and carboxymethyl starch; cellulose derivatives such as crystalline cellulose, hydroxypropyl cellulose, carboxymethyl cellulose, calcium carboxymethyl cellulose, sodium carboxymethyl cellulose; gum arabic; dextranum; silicate derivatives such as metasilicate magnesium aluminum; phosphate derivatives such as calcium phosphate; carbonate derivatives such as calcium carbonate; sulfate derivatives such as calcium sulfate, etc.), binders (e.g., gelatin, polyvinyl pyrrolidone, and polyethylene glycols), disintegrants (e.g., cellulose derivatives such as sodium carboxymethyl cellulose, polyvinylpyrrolidone), lubricants (e.g., talc, calcium stearate, magnesium stearate, spermaceti, boric acid, sodium benzoate, leucine), stabilizers (methyl parahydroxybenzoats, propyl p-hydroxybenzoate, etc.), flavoring agents (such as the commonly used sweeteners, sour agents and spices and the like), diluents and solvents for injections (such as water, ethanol and glycerol, etc.).

The administrating dosage of compounds of the present invention, pharmaceutically acceptable salts or prodrugs thereof, or the pharmaceutical compositions thereof varies with age, sex, race, and disease of the patients. Generally, the daily dose for adult is about 10 mg-2000 mg, and preferably 50 mg-1000 mg.

Cell Cycle Regulation

The present invention provides a method for regulating cell cycle which comprises administering an effective amount of the compound of Formula I or a pharmaceutical composition comprising a compound of Formula I to a subject cell.

Preferably, the compound of Formula I can be used to block the cell cycle, e.g., to induce the arrest of G1, G2 cycle of cells, thus adjusting the cell cycle of the cells, or change the procedure of cell division.

The compound of Formula I or the pharmaceutical composition thereof can be used to selectively regulate the cell cycle of some cells, while not inducing the block of cell cycle in other non-sensitive cells. In another preferred embodiment, the medicine or pharmaceutical composition is used to adjust cell cycle of tumor cells.

In another preferred embodiment, the cancer cell is selected from the group consisting of: Hela, H4, FHCC98, SMMC7721, BEL7404, A498, SW1116, MDA-MB-231, MDA-MB-468, DU145, U87-MG, Wi38, H1299, and combinations thereof; preferably is selected from the group consisting of: Hela, H4, FHCC98, SMMC7721, or combinations thereof.

The compound of Formula I can be used in a relatively low concentration, and preferably a concentration≤1 mM/L to cells so as to induce or adjust the cell cycle, thus blocking the cell cycle. In another preferred embodiment, the effective concentration of Formula I compound is 0.01 nM/L-1 mM/L, preferably 0.1 nM/L-500 µM/L, and most preferably 1 nM/L-100 µM/L.

Action period of the compound of Formula I is not particularly limited, and it can be e.g., for 2 h-30 days. Preferably, the affection time of the compounds of the Formula I varies depending on different environments and subjects. In a preferred embodiment of the present invention, the action period of compound of Formula I is 2-96 hrs. In another preferred embodiment, the action period of compound of Formula I is 1-30 days.

The Apoptosis Induction

The present invention provides a method for induction of apoptosis or inhibition of cell growth, which comprises administering an effective amount of the compound of Formula I or a pharmaceutical composition comprising a compound of Formula I to a subject cell.

The compound of Formula I or the pharmaceutical composition thereof can be used to induce the apoptosis of some cells or inhibit the growth of some cells, while not inhibiting the growth of other non-sensitive cells.

In another preferred embodiment, the medicine or pharmaceutical composition is used to adjust the cell cycle of tumor cells. Preferably, the cancer cell is selected from the group consisting of: Hela, H4, FHCC98, SMMC7721, BEL7404, A498, SW1116, MDA-MB-231, MDA-MB-468, DU145, U87-MG, Wi38, H1299, and combinations thereof; and the most preferable subject tumor cells are selected from the group consisting of: Hela, H4, FHCC98, SMMC7721, and combinations thereof.

The compound of Formula I can be used in a relatively low concentration, and preferably a concentration≤100 mM/L to subject cells so as to induce or adjust the cell cycle, thus providing block of cell cycle.

In another preferred embodiment, the effective concentration of Formula I compound is 0.01 nM/L-1 mM/L, preferably 0.1 nM/L-500 μM/L, and most preferably 1 nM/L-100 μM/L.

Action period of the compound of Formula I is not particularly limited and can be, e.g., for 2 h-30 days. Preferably, the affection time of the compounds of the Formula I varies depending on different environment and subjects. In a preferred embodiment of the present invention, the action period of compound of Formula I is 2-96 hrs. In another preferred embodiment, the action period of compound of Formula I is 1-30 days.

Antineoplastic Drugs (Pharmaceutical Compositions) and the Preparations Thereof

The present invention provides a method for induction of apoptosis or inhibition of cell growth, which comprises administering an effective amount of the compound of Formula I or a pharmaceutical composition comprising a compound of Formula I to a subject cells.

In a preferred embodiment of the present invention, the pharmaceutical compositions comprises: (a) a therapeutically effective amount of compound of Formula I; and (b) a pharmaceutically acceptable carrier.

In another preferred embodiment, the tumor comprises cervical cancer, glioma, or hepatocellular carcinoma.

In another preferred embodiment, the effective concentration of Formula I compound is 0.01 nM/L-1 mM/L, preferably 0.1 nM/L-500 μM/L, and most preferably 1 nM/L-100 μM/L.

The present invention further provides a method to prepare anti-tumor medicine or pharmaceutical composition, wherein the method comprises: mixing an effective amount of compounds of Formula I with a pharmaceutically acceptable carrier, thereby forming the pharmaceutical composition.

In another preferred embodiment, the composition further comprises the following ingredients: a tumor inhibitor, tumor apoptosis inducer, and combinations thereof.

Administrating to a subject a therapeutically effective amount of compound of Formula I or a pharmaceutical composition comprising a compound of Formula I can inhibit or treat tumors.

The Main Advantages of the Present Invention Include:

(1) the invention provides a good novel anticancer drug with low toxicity and safety,;

(2) the invention provides a method for highly selective induction of apoptosis;

(3) the invention provides a method for highly selective blocking of cell cycle;

(4) the invention provides a method for highly selective inhibition of cell migration;

(5) Anagrelide and its derivatives thereof in the present invention have very good anti-tumor effect. At relatively low doses (10 nM/L), Anagrelide can obviously inhibit the growth of tumor cells, while for non-sensitive cell lines, it does not have any growth inhibition effect even when the concentration was raised up to 1 mM/L, indicating that there is a strong specificity and selectivity for targets, thus having great application value and advantages in clinical application.

The present invention will be further illustrated below with reference to the specific examples. It should be understood that these examples are only to illustrate the invention but not to limit the scope of the invention. The experimental methods with no specific conditions described in the following examples are generally performed under the conventional conditions (for example, according to J. Sambrook et al., Molecular Cloning: A Laboratory Manual (New York: Cold Spring Harbor Laboratory Press, 1989)), or according to the manufacturer's instructions. Unless indicated otherwise, parts and percentage are calculated by weight.

EXAMPLE 1

The Effects of Anagrelide on Tumor Cells

1. General Experimental Materials and Methods 1.1 Medicine and Agents

Anagrelide was bought from J & K company, solved with dimethyl sulfoxide (DMSO) to formulate into 10 mM stock solution, and was kept under −20□. DMEM, a-MEM, PRMI1640 culture medium and fetal calf serum were bought from Gibco company (Life Technologies, Grand Island, N.Y., USA).

The antigens used in the research was as following: rabbit anti-PARP, bought from CST company, rat anti-tubulin, bought from Santa company.

1.2 Cell Lines and Cell Culture

TABLE 1

Sources of human tumor cell lines

| Cell line | Source | source of tissue | culture medium |
| --- | --- | --- | --- |
| H4 | ATCC | Human glioma cells | DMEM + 10% FBS |
| A498 | ATCC | Human kidney cancer cell | PRMI1640 + 10% FBS |
| SW1116 | ATCC | Human colon cancer cell | MEM + 10% FBS |
| HeLa | ATCC | Human cervical carcinoma epithelial cell | DMEM + 10% FBS |
| FHCC-98 | Cell Bank of Chinese Academy of Sciences | Human hepatoma carcinoma cell | PRMI1640 + 10% FBS |
| Bel7404 | Cell Bank of Chinese Academy of Sciences | Human hepatoma carcinoma cell | PRMI1640 + 10% FBS |
| SMMC7721 | Cell Bank of Chinese Academy of Sciences | Human hepatoma carcinoma cell | PRMI1640 + 10% FBS |

TABLE 1-continued

Sources of human tumor cell lines

| Cell line | Source | source of tissue | culture medium |
|---|---|---|---|
| DU145 | ATCC | Human prostate cancer cell | PRMI1640 + 10% FBS + 2 mM glutamine |
| U87-MG | ATCC | Human breast cancer cell | DMEM + 10% FBS |
| MDA-MB-231 | ATCC | Human breast cancer cell | PRMI1640 + 10% FBS |
| MDA-MB-468 | ATCC | Human breast cancer cell | PRMI1640 + 10% FBS |
| Wi38 | ATCC | Human lung cancer cell | DMEM + 10% FBS |
| H1299 | ATCC | Human lung cancer cell | PRMI1640 + 10% FBS |

Cell lines were placed in 37° C. cell incubator containing 5% $CO_2$, and the experiment was conducted when cells were in the logarithmic growth phase.

1.3 Western Blotting Analysis

1) Vertical electrophoretic separation of proteins: 8%-10% SDS-polyacrylamide (SDA-PAGE) gel electrophoresis separation, 5% stacking gel. The voltage for stacking gel was 80V, separation gel separation voltage for separating gel was 120V, and electrophoresis was stopped when bromophenol blue indicator ran to the bottom;

2) membrane transferring: semi-dry transferring: transmembrane voltage was 10-15V, and the time was adjusted according to the size of the protein;

3) pre-stained with Ponceau to observe transmembrane effect;

4) blocking: It was blocked with 5% skim milk in TBST and oscillated on Decolorization shaker at room temperature for 1 hour;

5) the binding with first antibody: The antibody was diluted at 1: 2000 to 1: 10000 in TBST containing 5% BSA, oscillated on decolorization shaker 1 hour under room temperature for binding, and placed at 4° C. overnight. TBST was used to wash for three times, and 10 minutes for each time.

6) the binding with secondary antibody: The antibody was diluted at 1:5000 to 1:10000 in TBST containing 5% BSA, and oscillated on decolorization shaker 1 hour for binding under room temperature. TBST was used to wash for three times, and 10 minutes for each time.

ECL developing kit was used to treat substrate for 2-3 minutes, detected for chemiluminescence, and exposed on X-ray film.

1.4 MTT (MTT) Colorimetry

Logarithmic growth phase cells were seeded in 96-well culture plate in appropriate density (100 μl in each well). After overnight cultivation, different concentrations of drugs were added and treated for 72 h, while three wells were set for each concentration. After treatment was completed, 20 μl/well of MTT (5 mg/ml in PBS) was added to each well and affected for 3-5 hours, the medium was suctioned out completely and 100 ul/well of DMSO was added, oscillated on decolorization shaker in dark place for 10 minutes until the Blue purple crystals formazan (formazan) was completely dissolved, the OD (Optical Density) value was detected with a microplate reader (detection wavelength: 595 nM; reference wavelength: 650 nM). In blank group, culture medium only added without cells, and in control group, DMSO in the same volume as that for drug was added. Cell viability was calculated=(OD value of experimental group–OD value of control group)/(OD value of control group–OD value of blank group).

1.5 Cell Cycle Distribution Detection by Flow Cytometry

Logarithmic growth phase cells were seeded in 6-well culture plate in $5\times10^5$/mL concentration, 1.5 mL of culture medium in each well, and cultured overnight. Different concentrations of drugs were added to stimulate for a certain time, and then the cells were collected into 1.5 mL EP tube. The cells were washed with cold PBS for 1-2 times, little PBS (about 200 ul) was added and blown to uniform. 1 mL 75% ethanol was pre-cooled (prepared with PBS), and cells was added dropwise into alcohol solution which was oscillated on shaker, fixed under 4° C. overnight. After 1000rpm centrifuged for 5 min, the supernatant was discarded and 1-2 mL PBS was added to wash twice. The cells were suspended with 0.5 mL RnaseA (1.0 mg/ml), and digested under 37° C. for 1 h. The cells were resuspended with 0.5 mL 25 ug/mL PI dye liquor, and were kept in dark place under 4° C. for 30 min. The cells were filtered with 300 mesh sieve, and the cell cycle distribution was analyzed with flow cytometry.

1.6 The Detection of Apoptosis by Annexin V/PI Double Staining

Logarithmic growth phase cells were seeded in 6-well culture plate in $5\times10^5$/mL concentration, and cultured overnight. Different concentrations of drugs were added for stimulation, the cells were collected, and apoptosis was detected by Annexin V/PI-FITC apoptosis detection kit commercially available from KGI biotech company. The specific steps were as follows: the cells were harvested into 1.5 mL centrifuge tube, and cells were washed twice with PBS. 500 ul of Binding Buffer was added to suspend the cells, and 5 ul of Annexin V-FITC was added to blend, and then 5 ul of PI was added to blend. The reaction was conducted under room temperature in dark place for 15 min. Apoptosis was detected by flow cytometry.

1.7 Monitoring Cell Growth with RTCA Cell Cytometry Real-time Monitor

Logarithmic growth phase cells were digested with trypsin, centrifuged and resuspended, and were seeded at $3.5\times10^4$ /mL per well in 16-well plate matching to cell supporting real-time monitor, and the compound was dosed after 37° C. overnight incubation. Real-time monitoring was used to automatically detect the status of cell growth, and the cell number was reflected by the size of the resistance formed after cell spreading. The larger the cell index value, the faster the cell growth, and the more the number of cells.

1.8 Cell Migration Detection via Scratch Experiment

The bottom of the six-well plate was uniformly marked with horizontal strips by marker, and then the logarithmic growth phase cells were seeded in the plate by $120\times10^4$ /mL concentration to make the cells evenly cover the six-well plate, and cells were incubated under 37° C. overnight. Fresh serum-free medium was changed, after the cells were starved for 10 hours, the bottom of six-well plate was scratched perpendicularly to horizontal strips, and washed three times with serum-free medium. After the suspended cells were rinsed, serum-free medium was added and photographed in 0, 2, 6, 12, and 24 hours. Image J was used to calculate the moving distance of the cells.

Figure 1:
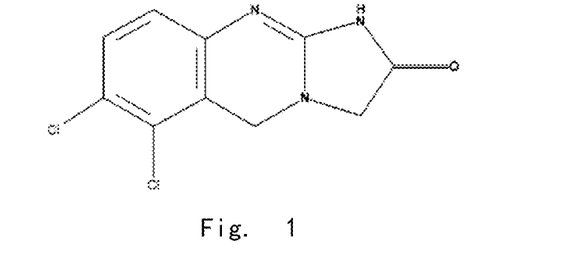
FIG. 1 shows the chemical structure of Anagrelide.

2. Experimental Results 2.1 The in vitro Anti-tumor Effect of Anagrelide on Tumors from Different Tissue Sources Through screening more than 500 kinds of listed FDA-approved non-anti-cancer drugs, the small molecule compound Anagrelide was discovered to possess inhibitory effect on tumor cells from various tissue sources. The formula of Anagrelide was 6,7-dichloro -1,5-dihydro-imidazo [2,1-b] quinazolin-2 (3H)-one (FIG. 1).

Tumor cells from different tissue source were selected, and the concentration of Anagrelide was 1 μM and 50 μM, OD value was MTT detected after administrated for 72 hours, and the cell viability was calculated using cell viability=(administered group OD-blank group OD)/(control group OD-blank group OD)*100%, and was mapped by using GraphPadPrism 4 software. The tumor spectrum obtained was shown in FIG. 2.

Figure 2:
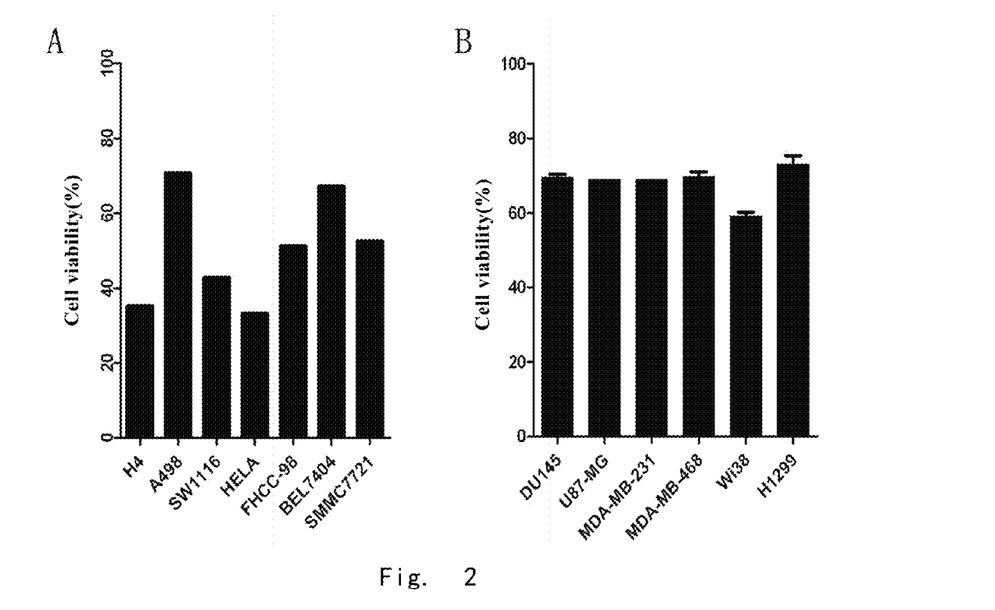

The results showed that Anagrelide significantly inhibited growth of Hela, H4, FHCC98, SMMC7721, BEL7404, A498, SW1116 cells when the concentration was 1 μM; and for MDA-MB-231, MDA-MB-468, DU145, U87-MG Wi38, H1299 cells, the Anagrelide inhibited their growth when the concentration was 50 μM.

2.2 The Different Anti-tumor Effects of Anagrelide on Different Tumor Cells

To further examine Anagrelide inhibition of cell growth, Hela, H4, FHCC98, SMMC7721, BEL7404, A498, SW1116 were taken for further experiment. Through cell real-time monitoring device, real-time monitoring of cell growth status change within 72 hours after Anagrelide administration was conducted (FIG. 3). 3000 cells/100 uL were plated, cultivated overnight, and 100 nM Anagrelide was added. The growth of cells was detected with real-time monitor. The red line showed the DMSO control group, while the green line showed the administration group.

Figure 3A:
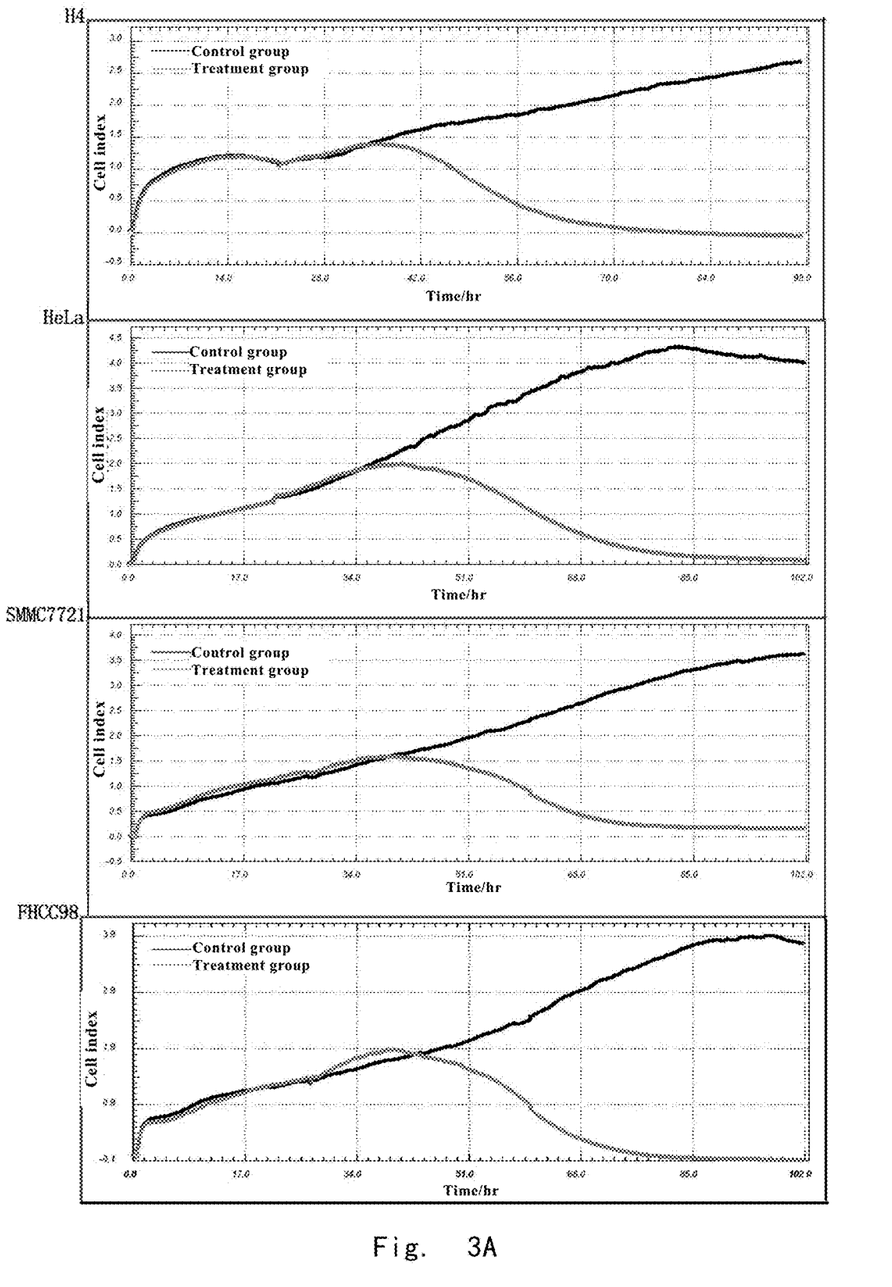
FIG. 3 shows the real-time detection results of cells and the IC50 value of Anagrelide on different cell lines; 3000 cells/100 uL were plated, cultivated overnight and 100 nM Anagrelide was added. A real-time monitor from Roche was used to detect growth of cells. The red line shows the DMSO control group, while the green line shows the administrating groups.
Figure 3B:
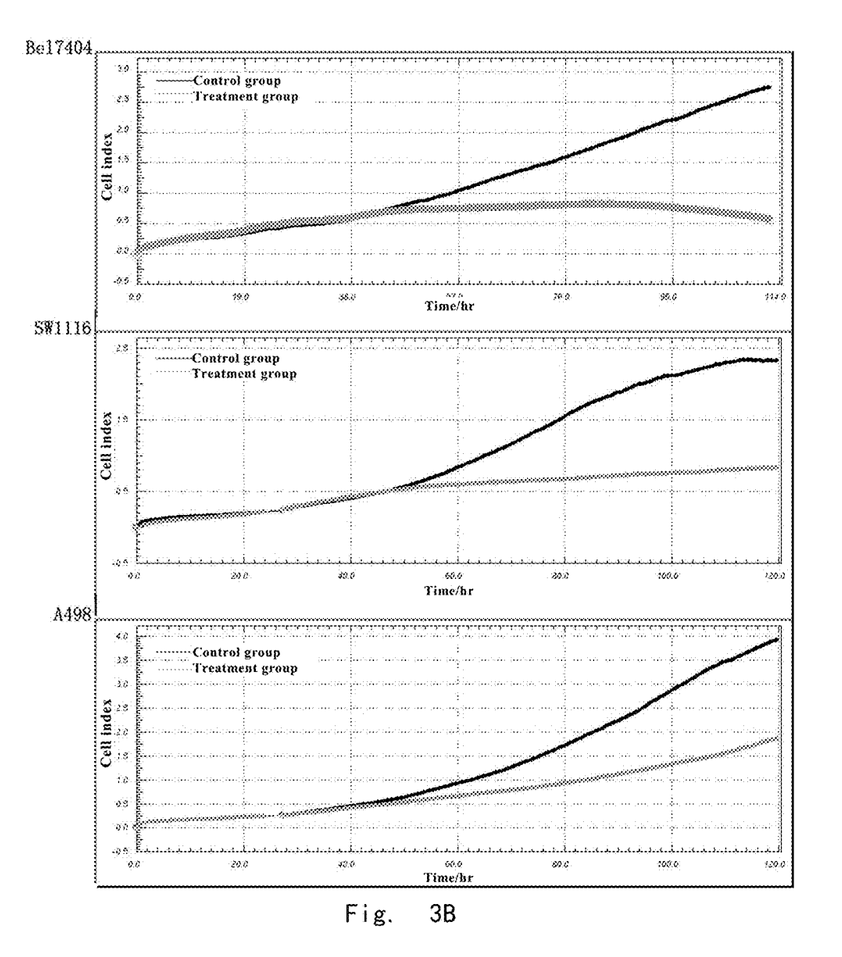

The results showed that for Hela, H4, FHCC98, and SMMC7721 cells (sensitive cells), Anagrelide ultimately induced the cell death, and for BEL7404, A498, and SW1116 cells (cells comparatively sensitive), the administration did not cause the cell apoptosis within 72 hours, but the growth was suppressed.

IC50 values on this seven cell lines of Anagrelide were detect by MTT method, and all of them are less than 100 nM (Table 2).

The results showed that the compounds of the present invention could inhibit the growth of various tumor cells at very low concentrations.

TABLE 2

| IC50 of Anagrelide to different cell lines | | | | | | | |
|---|---|---|---|---|---|---|---|
| Cell line | HeLa | H4 | FHCC98 | SMMC7721 | Bel7404 | A498 | SW1116 |
| IC50 (nM) | 5.121 | 5.433 | 7.076 | 2.006 | 32.76 | 52.99 | 40.58 |

2.3 The Effect of Anagrelide on Tumor Cell Cycle

Tumor cells are a type of cells whose cell cycle is not normally regulated, and they can be proliferate immortally. Some of the commonly used anti-tumor chemotherapy drugs in clinical practice have already been used as cell cycle retardant to inhibit tumor cell growth, thus achieving anti-tumor effect.

Figure 4:
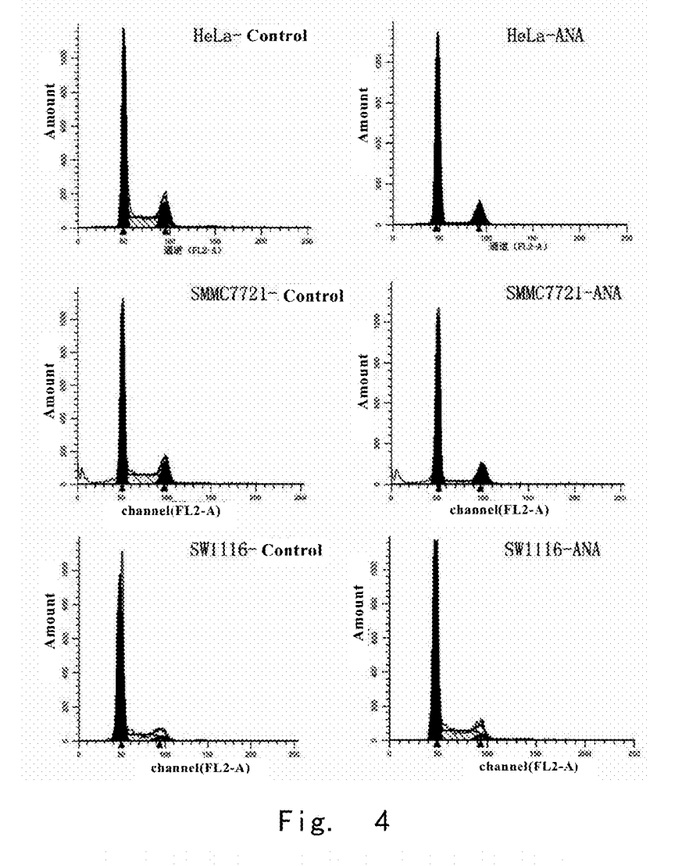
FIG. 4 shows the distribution of cell cycle detected by flow cytometry after 100 nM Anagrelide was administrated to cells for 24 hours.
Figure 5:
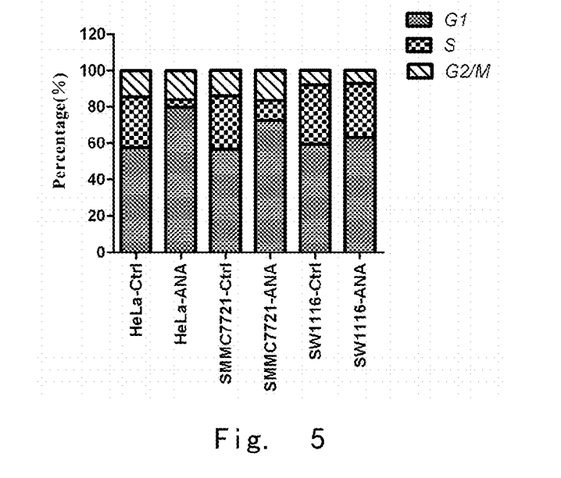
FIG. 5 shows the statistical diagram of the results detected by flow cytometry.

In order to determine whether Anagrelide had affected the cell cycle of tumor cells, SMMC7721, HeLa, SW1116 were taken as example to represent sensitive cells and relatively sensitive cells to detect the effect on cell cycle of Anagrelide by PI staining and flow cytometry (FIG. 4 and FIG. 5).

The results showed that as to SMMC7721 and HeLa cells treated with Anagrelide, cells in G1 phase and G2/M phase were increased significantly, while S phase cells were decreased, indicating that a significant G1, G2 cycle arrest was produced to the cells, while as to the relatively insensitive cell SW1116, Anagrelide produced a relatively weaker effect of cycle arresting.

2.4 Anagrelide Induces Tumor Cell Apoptosis

After observation, it was found that the cell size decreased after prolonged administration of Anagrelide, the cytoplasm was concentrated and ultimately dead. Therefore, H4 and FHCC98 cells were taken for example to detect effect of Anagrelide on apoptosis pathway by Western Blotting.

Figure 6:
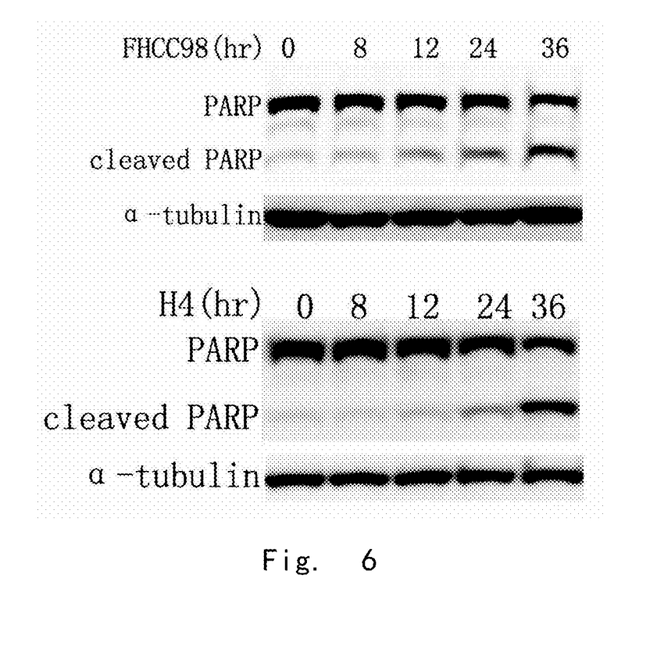
FIG. 6 shows the results of PARP cleavage via Western Blotting on the samples which were corrected at different times after 100 nM of drug concentration were administrated to H4 or FHCC 98 cells.

Western Blotting results were shown in FIG. 6. After the cells were treated with Anagrelide for a certain time, detection of downstream PARP cleavage was conducted and it was found that PARP cleavage was gradually increased with time. These results suggested that Anagrelide was capable of inducing apoptosis of tumor cells.

H4 cells and FHCC 98 cells were collected after drug administration at different time points, while the drug concentration was 100 nM. The PARP cleavage was detected by Western Blotting.

From the above experiments, it was seen that Anagrelide could induce cycle arrest in all the sensitive cells. For sensitive cells such as HeLa, H4, SMMC7721, FHCC98, the cycle arrest was very strong, the cells ultimately began apoptosis after cell growth was stopped for a period of time. Although relatively sensitive cells such as SW1116, A498 and Bel7404 cells were able to maintain slow growth, a significant cycle arrest phenomenon was produced, indicating that Anagrelide could also induce cycle arrest in those tumor cells.

2.5 Anagrelide Inhibited Tumor Cell Migration

Cell migration is a major characteristic of tumor cells. When the primary tumor has grown to a certain extent, it will gradually spread around to get more space and more nutrients to maintain the growth of tumor cells. Once the tumor cells diffuse in vivo, they will bring great difficulties for the treatment of tumors. Therefore, inhibiting tumor metastasis is a very important aspect in current anti tumor field.

By Scratching assay (HeLa cells were used as an example), the effect of Anagrelide on tumor cell migration was detected.

Figure 7:
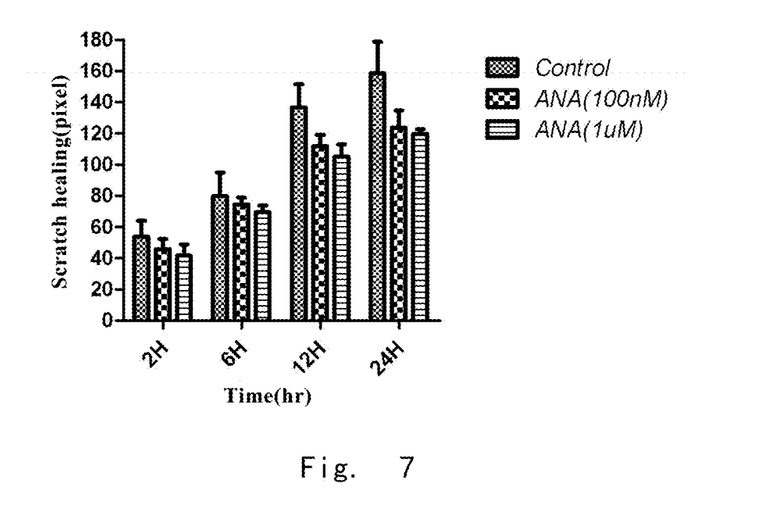
FIG. 7 shows the effect of Anagrelide on tumor cell migration.

The results were shown in FIG. 7. Anagrelide could significantly inhibit the healing speed of scratch in HeLa cells at 100 nM, which showed that Anagrelide could inhibit the migration of tumor cells.

3. The Antitumor Experiment of the Derivatives of Anagrelide

The inventor repeated the above experiments with a series of Anagrelide derivatives, and the similar results of hydrochloride salt of Anagrelide were obtained. The derivatives of Anagrelide used in the experiments were as follows:

EXAMPLE 2

The Effect of Anagrelide on Human H4 Transplantation Tumor

1. Materials and Method
1.1 Materials
1.1.1 Test Samples
Name: Anagrelide
Catalog number: A637300
Appearance: white powder
Purity: 98%
Source: Toronto Research Chemicals Ins.
Preservation: preserved under −20 □ before preparation
1.1.2 Negative Control (Vehicle)
Cremophor EL: 95% Medicinal ethanol: water=12.5:12.5:75

Cremophor EL was bought from Sigma, Catalog number C5135; 95% medicinal ethanol was bought from Shanghai Yichun Biotechnology Co., Ltd.

1.1.3 Experimental Animal
BALB/c naked mouse, female, body weight 16-17g, bought from SHANGHAI SLAC LABORATORY ANIMAL CO. LTD (license number: SCXK (Shanghai) 2012-0002), Living environment: SPF-class animal room, free feeding, 12 h light/12 h darkness.

1.2 Experimental Procedure
Under aseptic conditions, tumor cells in the proliferation stage were taken. The cell concentration was adjusted after digestion, seeded at right armpit of nude mice, and the inoculated volume was 0.1 mL. Tumor diameter was measured with vernier caliper, after the tumor was grown to 200-300 $mm^3$, the tumor-bearing mice were selected, and randomly divided into 3 groups (n=4) according to the size of the tumors: negative control group, Anagrelide I (10 mg/kg), Anagrelide II (30 mg/kg). Each group was intragastric administrated, the day of administration was recorded as d1, the negative control group was given same amount of vehicle, and then the long and short diameters of tumor were measured twice a week, while the body weights of mice were weighed. At the 21th day of the administration, the animals were sacrificed and the tumor was dissected and weighed. Before the animals were sacrificed, eyeball was taken for blood sample, the number of white blood cell (WBC), red blood cell (RBC), concentration of hemoglobin (Hb) and number of platelet (PLT) were measured.

Figure 8:
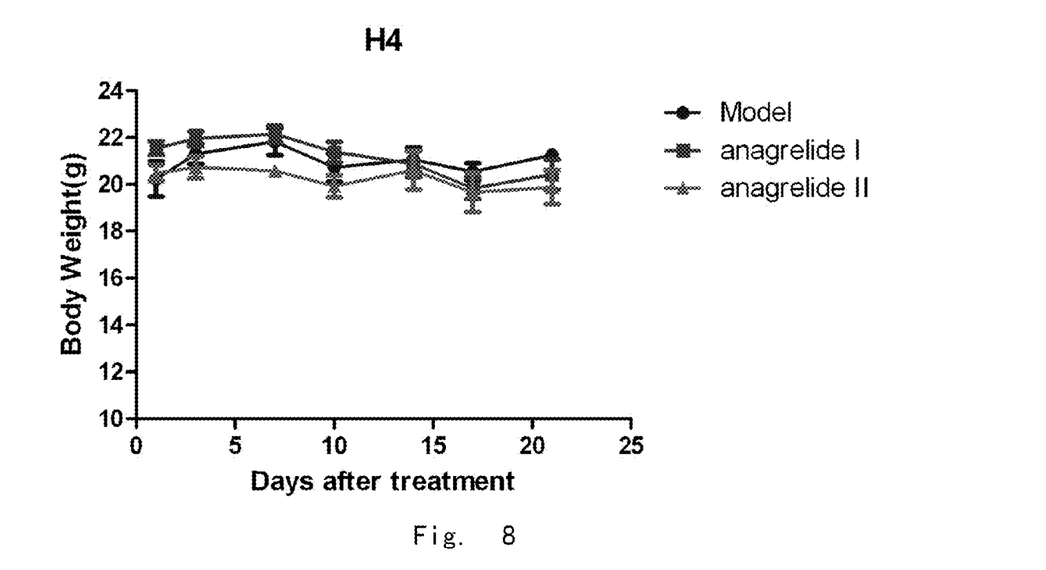
FIG. 8 shows the effect of Anagrelide on body weight of tumor-bearing nude mice.

2. Experimental Results
2.1 The Effect of Anagrelide on the Body Weight of Tumor-bearing Nude Mouse According to the weight change trend of animals from each treatment group, the effect of Anagrelide in each dose group to animal weight was little (FIG. 8), and there was no significant difference from the negative control group.

2.2 The Effect of Anagrelide on the Tumor Growth of Tumor-bearing Nude Mice

Figure 9:
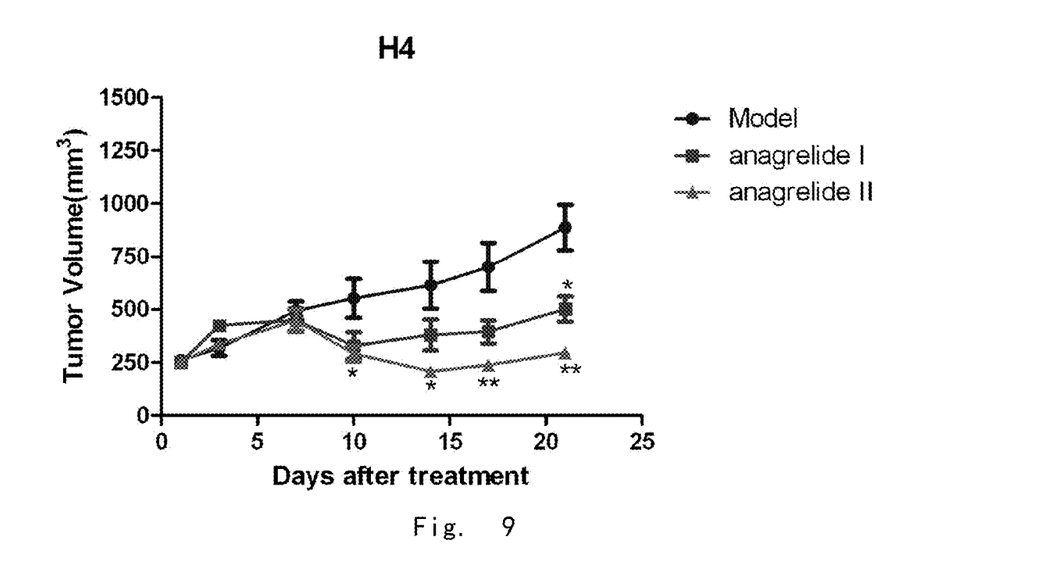
FIG. 9 shows the effect of Anagrelide on the tumor volume of tumor-bearing nude mice.
Figure 10:
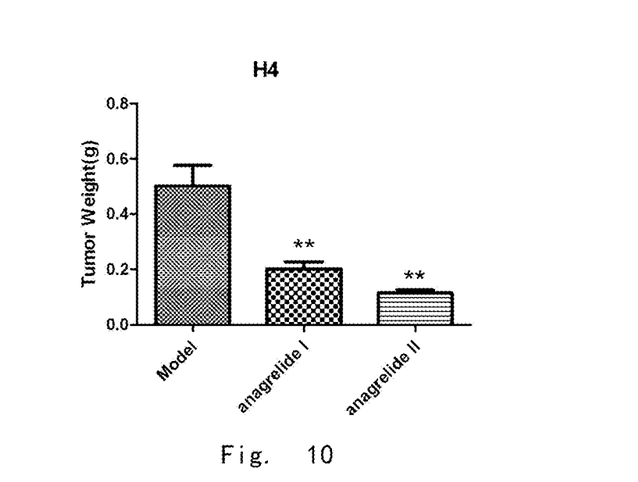
FIG. 10 shows the effect of Anagrelide on the tumor weight of tumor-bearing nude mice.

Compared with the vehicle control group, the treatment groups showed significant anti-tumor effect, and there was in a dose-concentration-dependent manner (FIGS. 9 and 10).

By the end of the experiment, the tumor weight of each treatment group was significantly lower than that of the vehicle control group, and tumor weight of Anagrelide II (30 mg/kg) group was less than that of Anagrelide I (10 mg/kg) group, which showed that the effect of Anagrelide on tumor weight was in a dose-dependent manner.

Figure 11:
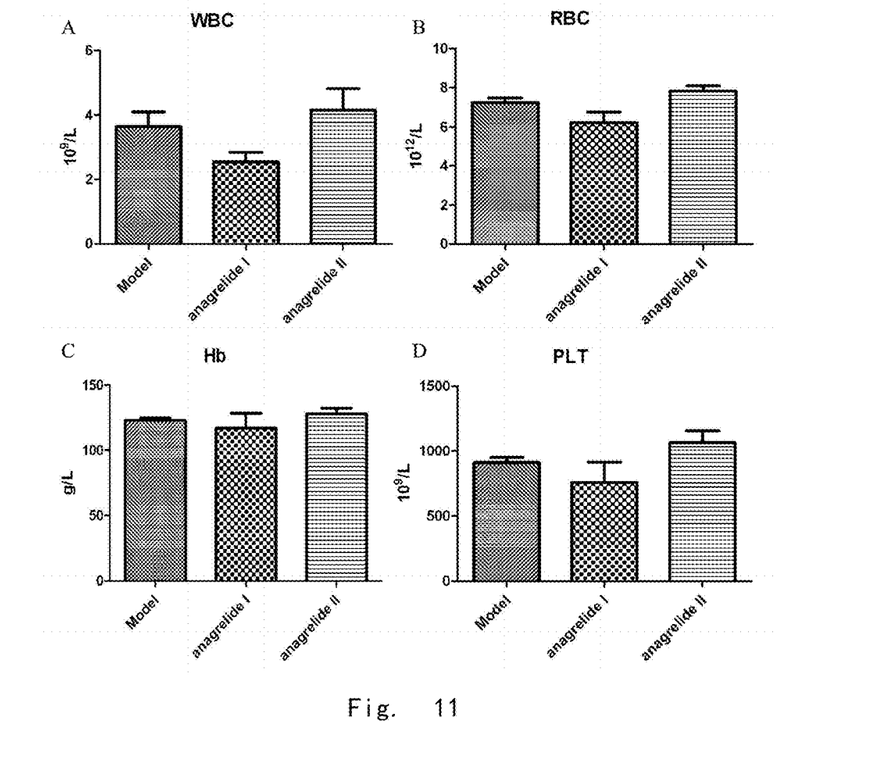

2.3 The Effect of Anagrelide on the Blood Routine Test of Tumor-bearing Nude Mice Compared with the vehicle control group, the blood routine test index of each treatment group blood didn't show any significant decrease (FIG. 11).

Discussion

Anagrelide has already been used on the market in the United States as an anti thrombocytosis drug for 16 years. Till now, there is no serious side effect of this drug. After screening, the inventors have unexpectedly discovered and confirmed that, Anagrelide has a good anti-cancer activity, and can inhibit the cell cycle of cancer cells at very low concentrations, and finally induce cancer cell apoptosis.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A method for inhibition of tumor and/or inhibition of growth of a tumor cell, comprising administering a compound of Formula (I), an optical isomer thereof, or a pharmaceutically acceptable salt thereof to a subject in need thereof to inhibit tumor or growth of a tumor cell;
wherein the Formula (I) is and
the tumor is a cancer selected from the group consisting of liver cancer, cervical cancer, glioma, colon cancer, kidney cancer, breast cancer, lung cancer, and prostate cancer.

2. The method of claim 1, wherein the pharmaceutically acceptable salt is a salt of an acid that is hydrochloride, acetate, phosphate, or a combination thereof.

3. The method of claim 1, wherein the pharmaceutically acceptable salt is a salt of hydrochloride.

4. The method of claim 1, wherein the compound of Formula (I) induce induces tumor cell apoptosis.

5. The method of claim 1, wherein the compound of Formula (I) disturbs tumor cell proliferation.

6. The method of claim 1, wherein the compound of formula (I) regulates cell cycle of a tumor cell; and/or the compound of Formula (I) blocks cell cycle of a tumor cell; and/or the compound of Formula (I) inhibits tumor cell metastasis.

* * * * *